(12) United States Patent
Rapp (10) Patent No.: US 11,191,796 B2
(45) Date of Patent: Dec. 7, 2021

(54) NOZZLES FOR ESSENTIAL ELEMENT EXTRACTION METHOD AND APPARATUS

(71) Applicant: Robert James Rapp, San Jose, CA (US)

(72) Inventor: Robert James Rapp, San Jose, CA (US)

( * ) Notice: Subject to any disclaimer, the term of this patent is extended or adjusted under 35 U.S.C. 154(b) by 62 days.

(21) Appl. No.: 16/371,540

(22) Filed: Apr. 1, 2019

(65) Prior Publication Data
US 2019/0328806 A1    Oct. 31, 2019

Related U.S. Application Data

(60) Provisional application No. 62/626,257, filed on Feb. 5, 2018.

(51) Int. Cl.
| | | |
|---|---|---|
| *A61K 36/00* | (2006.01) | |
| *A61K 36/185* | (2006.01) | |
| *B01D 11/02* | (2006.01) | |
| *B01D 11/00* | (2006.01) | |

(52) U.S. Cl.
CPC ........ *A61K 36/185* (2013.01); *B01D 11/0207* (2013.01); *B01D 11/0219* (2013.01); *B01D 11/0296* (2013.01); *B01D 2011/007* (2013.01)

(58) Field of Classification Search
None
See application file for complete search history.

(56) References Cited

U.S. PATENT DOCUMENTS

| 7,344,736 | B2 * | 3/2008 | Whittle | B01D 11/0203 |
| | | | | 424/725 |
| 9,327,210 | B1 * | 5/2016 | Jones | B01D 11/0215 |
| 9,358,259 | B2 * | 6/2016 | Hospodor | B01D 11/0292 |
| 2012/0263804 | A1 * | 10/2012 | Hospodor | A61P 25/04 |
| | | | | 424/725 |
| 2013/0251824 | A1 * | 9/2013 | Hospodor | B01D 11/0292 |
| | | | | 424/725 |
| 2014/0113010 | A1 * | 4/2014 | Hospodor | B01D 11/0292 |
| | | | | 424/725 |
| 2014/0129307 | A1 | 5/2014 | Walker | |
| 2016/0201009 | A1 * | 7/2016 | Lopez | A61K 36/63 |
| | | | | 554/9 |

OTHER PUBLICATIONS

Aladic et al. (2014) Chemical and Biochemical Engineering Quarterly 28(4): 481-490. (Year: 2014).*
Aladic et al. (2015) Industrial Crops and Products, 76: 472-478. (Year: 2015).*
Raskin et al. (2004) Current Pharmaceutical Design, 10, 3419-3429. (Year: 2004).*
Revilla et al. (1998) J. Agric. Food Chem. 46: 4592-4597. (Year: 1998).*
Visentin et al. (2011) Innovative Food Science and Immerging Technologies, 12: 142-145. (Year: 2011).*

* cited by examiner

*Primary Examiner* — Russell G Fiebig
(74) *Attorney, Agent, or Firm* — Robert J Rapp (57) ABSTRACT

The present disclosure includes a nozzle and methods for using the nozzle in ways that may increase the efficiency of extraction of essential elements from plant matter. The nozzle may also be used to increase the efficiency of drying solvent saturated plant matter after an extraction has been completed. The nozzle may include an elongated tube with a plurality of holes that allow solvent and/or a gas to be provided or pumped/provided into an apparatus that includes plant matter. Nozzles consistent with the present disclosure may be optimized for extracting cannabis from cannabis plant matter or from other types of plants that include cannabinoids. In certain instances, nozzles may also be used when processing cannabinoid containing concentrates that were extracted from plant matter using any type of extraction technique.

18 Claims, 9 Drawing Sheets

NOZZLES FOR ESSENTIAL ELEMENT EXTRACTION METHOD AND APPARATUS

CROSS REFERENCE TO RELATED APPLICATIONS

The present application claims priority benefit of U.S. provisional patent application 62/626,257, filed on Feb. 5, 2018, the disclosure of which is incorporated by reference into the present application.

FIELD OF THE INVENTION

The present disclosure is directed to advancing the state of the art of equipment and processes for extracting essential elements efficiently from plant matter in both large and small volumes. More specifically, the present disclosure is directed to methods and systems for extracting essential elements from plant matter that use specially designed nozzles.

BACKGROUND OF THE INVENTION

Advancing the state of the art of equipment and processes for extracting essential elements efficiently from plant matter in both large and small volumes will be in increasing demand in the future. This is especially true in instances when those essential elements do not readily dissolve in water, such as cannabinoids, terpenes, or flavonoids associated with the cannabis plant.

One common type of system for extracting essential elements from plant matter use carbon dioxide ($CO_2$). Such $CO_2$ extraction systems typically require both high temperatures and pressures to perform an extraction. In certain instances these high temperatures and pressures may be dangerous to persons that are in close proximity to such a $CO_2$ extraction system. One limitation related to $CO_2$ extracting systems is that they have a limited ability to scale. This is because as the size of a $CO_2$ extraction system is increased linearly, cycle times associated with performing an extraction also increases linearly. Another limitation associated with $CO_2$ extraction systems is that their efficiency reduces dramatically when plant matter being extracted has not been dried before an extraction. For example, a $CO_2$ extraction of un-dried plant matter may take up to ten times longer to perform as compared to a similar extraction using dried plant matter. As such, one must dry plant matter thoroughly in order to optimize the efficiency of a $CO_2$ extraction system, yet the drying of plant matter requires significant amounts of energy. Because of these reasons $CO_2$ extraction systems are not highly efficient and are not optimally environmentally friendly.

In recent years many states have legalized the medicinal use of cannabis, the recreational use of cannabis, or both. Because of this, vast amounts of cannabis plant matter will be grown throughout the United States for both medical and recreational consumption. Since many who wish to consume cannabinoids do not want to smoke plant matter, yet instead wish to consume cannabinoids orally or by using a suppository. Because of this, demand for extracting cannabinoids and other components included in cannabis will increase over time.

Another trend that has increased in recent years is an increasing use of explosive gasses for extracting cannabinoids from cannabis plant matter in households of individuals. Butane is one example of an explosive gas that is being commonly used to extract cannabinoids in personal homes. This trend has caused a significant increase in household fires because a small spark can cause such explosive gasses to rapidly ignite and burn. Commonly, such home extractions use small amounts of cannabis plant matter, perhaps weighing less than one ounce. Furthermore, explosive gasses such a butane, propane, or butane/propane combinations have been used in medium to larger scale extraction apparatus. As extraction apparatus that use Butane or propane will typically use high pressure explosive gasses in a liquid state, as those apparatus increase in size, wall thicknesses requirements associated with such apparatus increase in a non-linear fashion. As such, larger systems that use liquefied explosive gasses will become heavy and unwieldy. The use of explosive gasses has caused an increase in household fires and fires at extraction facilities that are focused commercial extraction.

What are needed are extraction systems that provide increased efficiency with size (i.e. that scale to industrial size), systems and methods that increase the safety of extraction, systems and methods that extract essential elements from plant matter and to remove residual solvent from plant matter using improved drying techniques. Methods that allow small growers and large cultivation operations to safely and efficiently extract essential elements from plant matter are needed. Furthermore, benefit may be gained by limiting or eliminating the use of explosive solvents (solvents like butane or propane that are in a gaseous state at room temperature/pressure and that may be in a liquid state at high pressures). What are also needed are apparatus that increase the efficiency of extraction operations.

SUMMARY OF THE DISCLOSURE

The presently disclosure reviews apparatus and methods for extracting essential elements from plant matter. In certain instances, cannabinoids may be extracted from cannabis plant matter or from other plant matter using specially designed nozzle. A method consistent with the present disclosure may include filling at least a portion of a vessel with plant matter, the vessel may include a nozzle that includes one or more surfaces with one or more hole for passing a fluid from an inside portion of the nozzle to an outside portion of the nozzle when an element from the plant matter. A liquid solvent may be introduced into the vessel, where the liquid solvent covers at one of the holes in the nozzle. Next either liquid solvent or the fluid may be moved through the nozzle after which a portion of an eluate may be passed from the inside of the vessel to the outside of the vessel via an output port. In instances the eluate may include a mixture of cannabinoids and solvent.

Another method consistent with the present disclosure may include introducing a cannabinoid containing substance into a vessel, introducing a first solvent into the vessel, and introducing a fluid into the vessel through a nozzle that includes one or more holes.

After an extraction is complete, the nozzle may also pass gas that dries solvent saturated plant matter after the vessel has been drained. Methods consistent with this disclosure may include one or more surfaces that include one or more holes for passing a gas from an inside portion of the nozzle to an outside portion of the nozzle when the element is extracted from the plant matter.

A nozzle consistent with the present disclosure may include one or more surfaces that include one or more holes for passing a gas from an inside portion of the nozzle to an outside portion of the nozzle when the element is extracted from the plant matter, where at least one of the one or more holes are immersed in a liquid solvent contained in a vessel.

The vessel may also containing the plant matter that is immersed in the liquid solvent, and an input coupled to at least one of a source of the gas or a vacuum pump.

Furthermore, nozzles for extracting an element from plant matter, the nozzle may include one or more surfaces that includes one or more holes for passing a liquid (gas, liquid, or both) from an inside portion of the nozzle to an outside portion of the nozzle when the element is extracted from the plant matter, when at least one of the one or more holes are immersed in a liquid solvent contained in a vessel. The vessel may also contain the plant matter, where the plant matter is immersed in the liquid solvent. An input may be coupled to at least one of a source of a gas, a vacuum pump, or a solvent pump, where at least one of the vacuum pump recirculates a portion of the gas or the solvent pump recirculates a portion of the liquid solvent through the nozzle.

Methods consistent with the present disclosure may include filling at least a portion of a vessel with plant matter, introducing a liquid solvent into the vessel, wherein the liquid solvent covers at least one of the one or more holes in a nozzle, pumping with at least one of a gas or a portion of the liquid from an output of the vessel to an input of the vessel through the nozzle, and draining at least a portion of the solvent from the vessel. The nozzle may also pass gas that dries solvent saturated plant matter after the vessel has been drained. Methods consistent with this disclosure may include one or more surfaces that include one or more holes for passing a gas from an inside portion of the nozzle to an outside portion of the nozzle when the element is extracted from the plant matter. The a fluid provided to a chamber may include a cryogenic liquid like liquid nitrogen.

DETAILED DESCRIPTION

Extraction and/or Drying Nozzles Apparatus and Methods:

The present disclosure includes a nozzle and methods for using the nozzle in ways that may increase the efficiency of extraction of essential elements from plant matter. The nozzle may also be used to increase the efficiency of drying solvent saturated plant matter after an extraction has been completed. The nozzle may include an elongated tube with a plurality of holes that allow solvent and/or a gas to be provided or pumped/provided into an apparatus that includes plant matter. Nozzles by distributing dry gas through solvent saturated plant matter may cause solvent to evaporate from plant matter more uniformly. Vaporized solvent may then be caught in a solvent trap, such as a Wolfe bottle or chilled condenser.

In yet other instances, a vessel may have a series of holes along one or more internal surfaces where gas is provided along the internal surfaces where the holes reside. One or more nozzles may also be inserted through the one or more holes during an extraction or a drying process.

While some nozzles consistent with the present disclosure may pass solvent that is liquid at room temperature/pressures, such as alcohol, hexane, or heptane or pass gasses that are not in themselves flammable (nitrogen or $CO_2$), nozzles consistent with the present disclosure may be used to pass gasses and/or liquids such as butane that are in a vapor state at room temperatures/pressures or that are liquid at higher pressures in systems that are designed to mitigate risks associated with explosive gasses. While nozzles passing non-flammable gasses may be preferred, in certain instances, gasses that include or are comprised of oxygen may be used, or other gasses such as nitrogen may be used.

Embodiments of the nozzle include: a nozzle that is longer than it is wide in at least one cross-section. The nozzle may be cylindrical in shape, may be in a cork-screw shape, may be cone shaped, may be in the shape of a conical spiral where the diameter circumscribed by the nozzle changes (increases or decreases) over the length of the nozzle. Even nozzles that withdraw when the pressure differential abates may be of any of these shapes. Some shapes, such as the cork-screw shape may be screwed or "drilled" into plant matter when deployed manually inserted into/through plant matter or when deployed/extended/retracted using linear or rotational motion via an automated system.

In certain instances nozzles may be deployed or retracted via pneumatic actuators or via motors. Pneumatic nozzle motion control may be implemented using various gasses, such as nitrogen or carbon dioxide, even so even gasses such as ambient air or gasses that include oxygen may be used. Alternatively nozzles may be deployed using an oil that may include hemp seed oil. In order to limit risks related to fire, explosion proof motors or gasses that do not include oxygen may be used.

Figure 1:
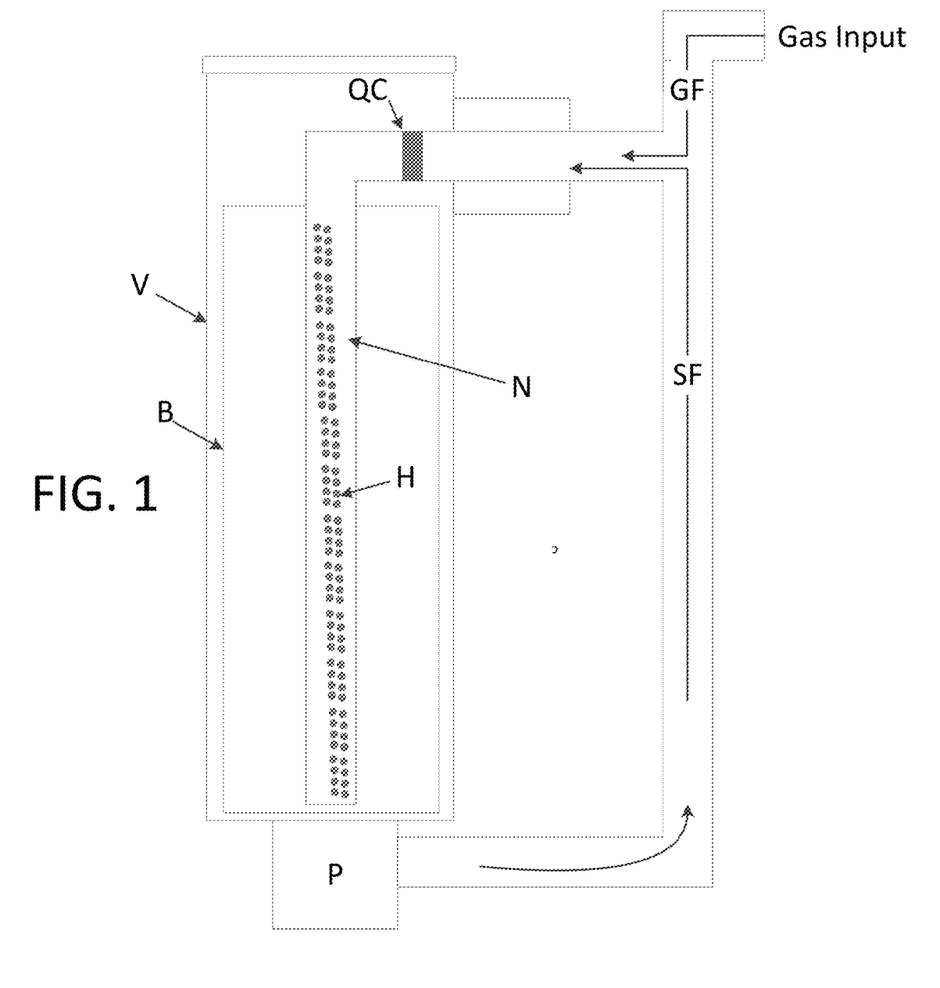
FIG. 1 illustrates an embodiment of a nozzle mounted in a vessel. Vessel V may be used to extract essential elements from plant matter.

FIG. 1 illustrates an embodiment of a nozzle mounted in a vessel. Vessel V may be used to extract essential elements from plant matter. FIG. 1 includes Vessel V, a basket B, a nozzle N, a gas input, and a solvent pump. Note that nozzle N includes a quick connect and many holes H. Note that gas flow GF may flow into the gas input and that the solvent pump may pump a flow of solvent SF through the nozzle. Note also that basket B may include plant matter. The nozzle N of FIG. 1 may, thus pass both solvent and gas into vessel V through nozzle N when essential elements are extracted from the plant matter. Such an apparatus may be used to extract essential elements from cannabis plant matter or may be used to extract cannabinoids from other plant types.

Figure 2:
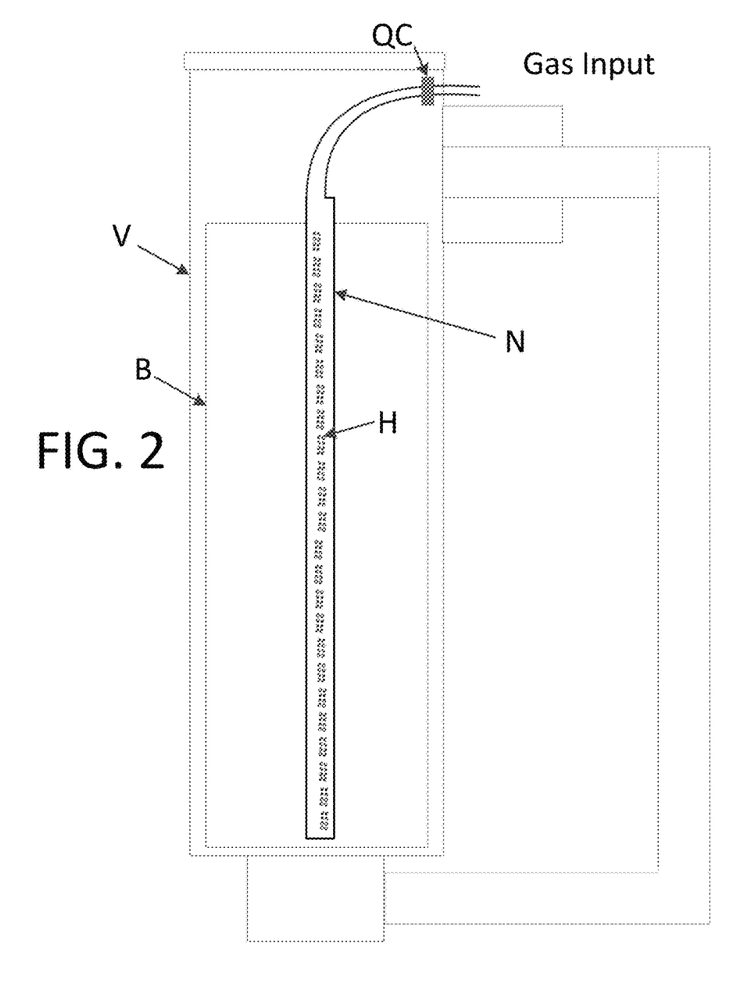
FIG. 2 illustrates an embodiment of a nozzle mounted in a vessel.

FIG. 2 illustrates an embodiment of a nozzle mounted in a vessel. FIG. 2 includes vessel V, basket B, nozzle N. The nozzle of FIG. 2 also includes holes H and quick connect QC where gas may flow into the vessel V through a gas input. Note that the gas input and nozzle N of FIG. 2, unlike the nozzle of FIG. 2 passes gas and not solvent. Alternatively, only liquid solvent may be passed through nozzle N.

Figure 3:
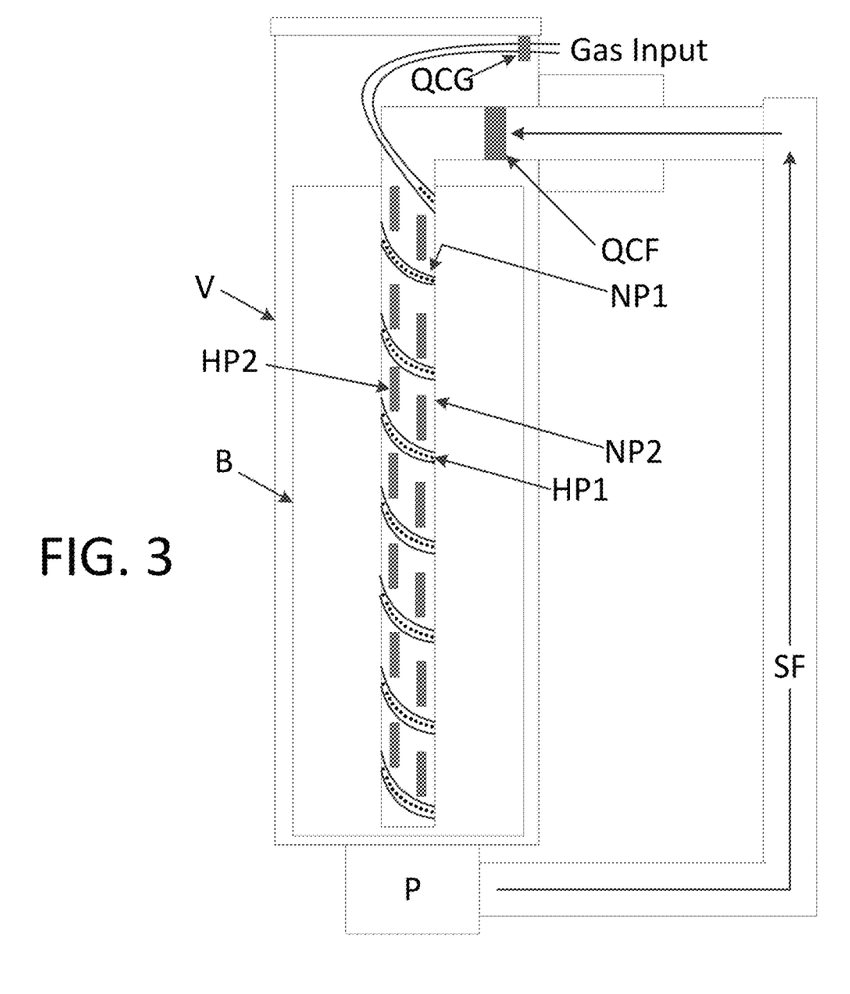
FIG. 3 illustrates a two part nozzle consistent with the present disclosure installed in a vessel.

FIG. 3 illustrates a two part nozzle consistent with the present disclosure installed in a vessel. FIG. 3 includes a vessel V that includes a nozzle with two parts NP1 and NP2, a gas input, and quick connects QC. Note that nozzle part NP1 includes circular holes HP1 and the nozzle part NP1 is attached to a gas input with a quick connect. Nozzle part NP2 in FIG. 3 includes holes HP2, where holes HP2 are rectangular shaped holes (i.e. slots). Nozzle part NP1 transfers gas from the gas input where nozzle part NP2 transfers solvent from pump P. A flow of recirculating solvent from pump P is depicted by the arrow labeled SF. Quick connect QCF in FIG. 3 is a quick connect used to connect the solvent nozzle part NP1 to a recirculating solvent SF. The two art nozzle including parts NP1 and NP2 is capable of delivering solvent and a gas (like nitrogen) into vessel V through two different paths. As soon as solvent and gas escape the nozzle, the may mix when extracting essential elements from plant matter included in basket B of FIG. 3.

Figure 4:
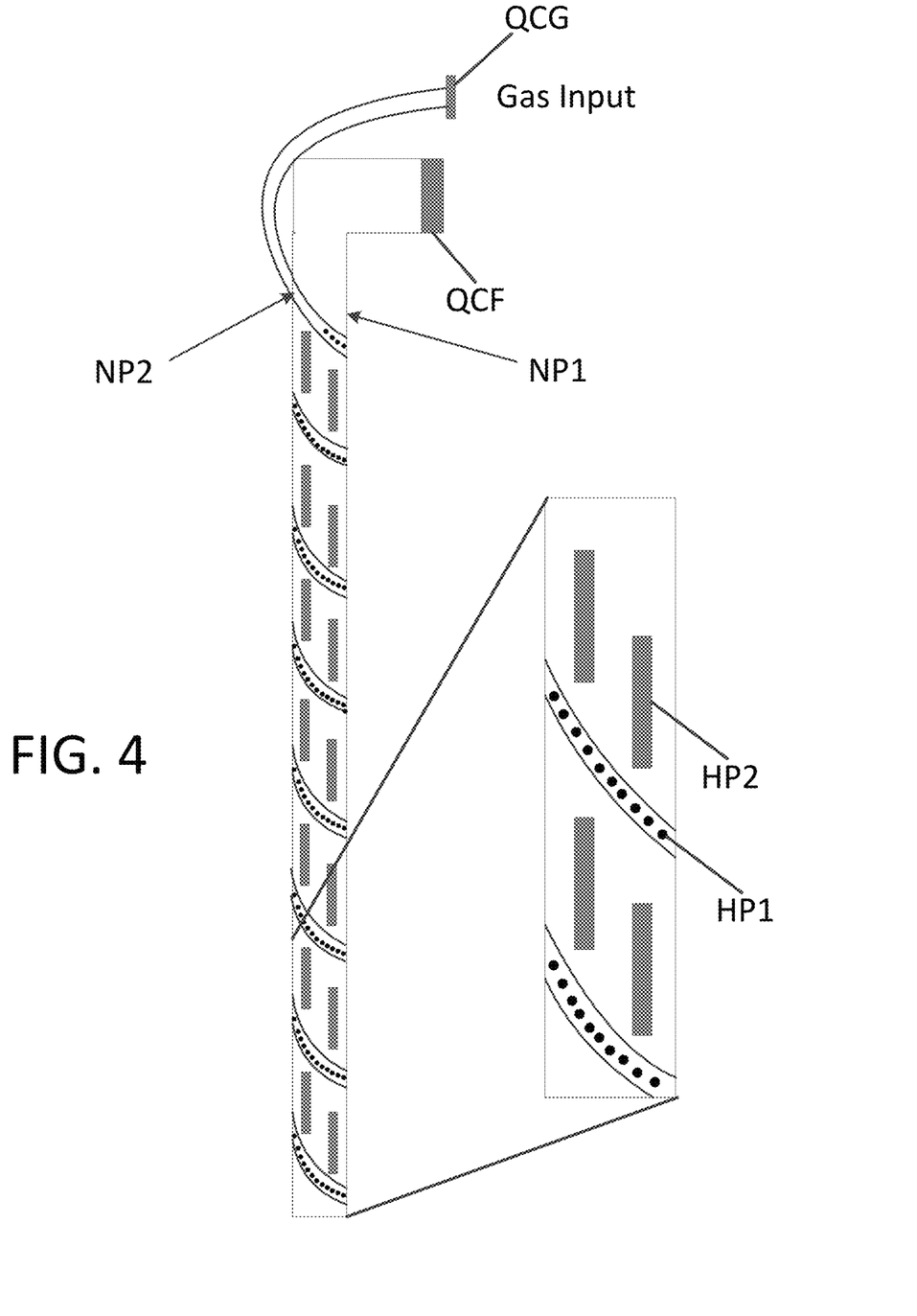
FIG. 4 illustrates the two part nozzle illustrated in FIG. 3.

FIG. 4 illustrates the two part nozzle illustrated in FIG. 3. The two part nozzle includes a first part NP1 for delivering solvent, a second part NP2 for delivering a gas. Here again the nozzle includes quick connect QCG through which a gas may be provided and quick connect QCF through which solvent may be provided. An expanded view of the two part nozzle depicts holes HP1 and HP2 through which gas and solvent may be respectively provided. Note that holes HP1 are circular and the holes HP2 are rectangular. Holes in nozzles may be of any shape or size. The nozzle may be fabricated from a variety of materials, preferably materials that are approved for contact with food by the U.S. Food and Drug Administration (FDA), such as stainless steel and/or Teflon based material (like PTFE). Note that nozzle part NP1 migrates around nozzle part NP2 like a corkscrew. Nozzle part NP2 may wrap around nozzle part NP2 providing a surface that extends away from nozzle part NP2 that is capable of being screwed into or out of plant matter.

The gas provided through the nozzle may also be used to actuate or move the nozzles from at least one position to at least one other position. In such instances, the nozzles may actuate when there is a pressure differential between an inner point (with a higher pressure) of the nozzle as compared to an outer point of the nozzle (at a lower pressure). In such instances the nozzles may be contained within an apparatus that includes internal parts that used to facilitate the movement of the nozzles. The nozzle may be spring loaded such that it actuates (pushes outward) into plant matter and then retracts. The nozzle may deploy using gas pressure. Nozzles may also be provided in configurations where they retract or extend using gravity.

Figure 5:
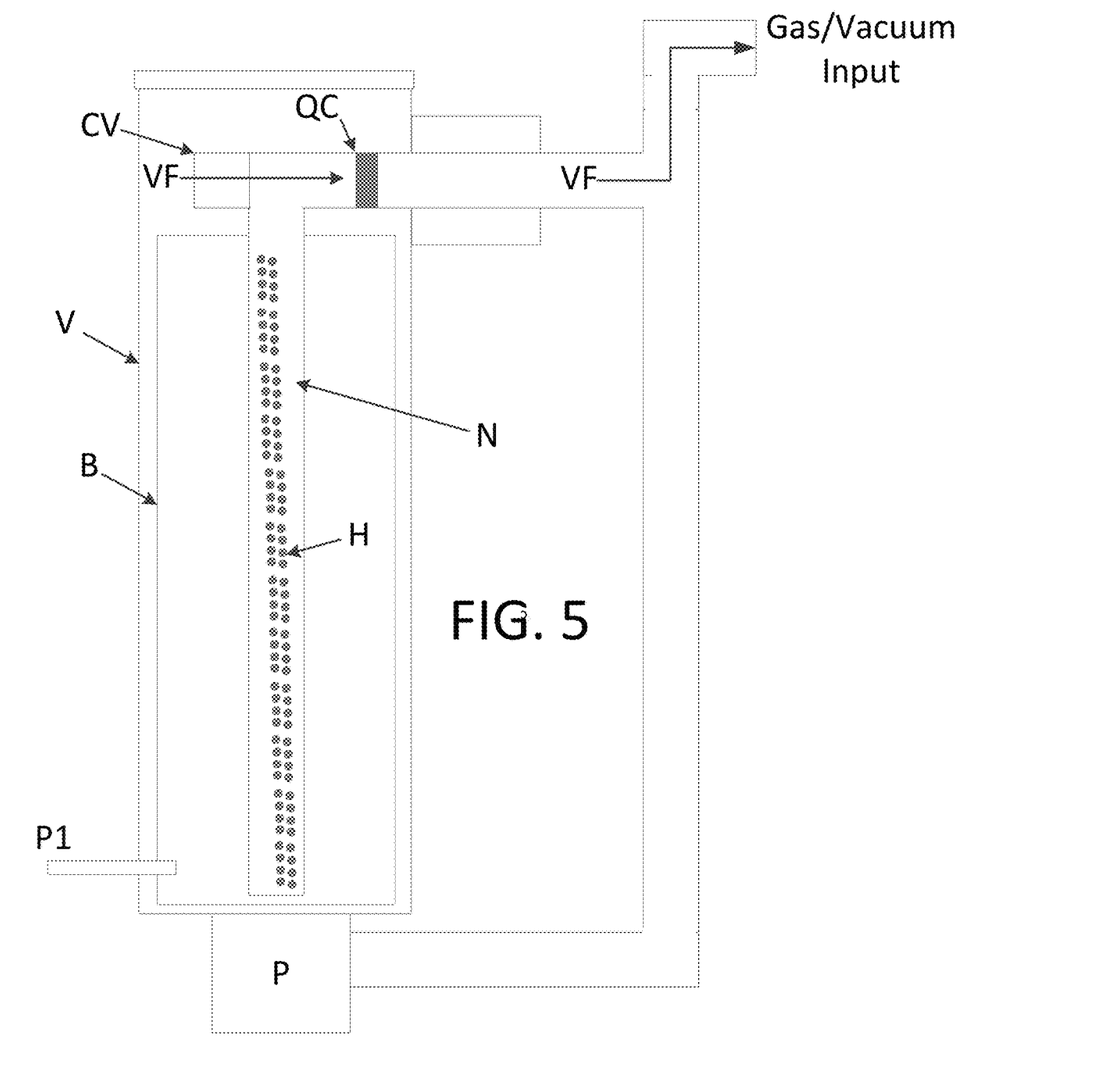
FIG. 5 illustrates a vessel including a nozzle that is connected to a gas/vacuum input.

FIG. 5 illustrates a vessel including a nozzle that is connected to a gas/vacuum input. FIG. 5 includes vessel V, basket B, nozzle N, quick connect QC, a check valve CV, and pump P. The gas/vacuum input of FIG. 5 includes a flow VF. In practice basket B may filled with plant matter and vessel V may be predominantly filled with liquid solvent, typically below the level of check valve CV. Vessel V also includes a prime input PIN through which liquid solvent may be introduced into vessel V. Vessel V may be primed with vacuum is applied to gas/vacuum input where liquid solvent flows into vessel V through prime input PIN. After extraction liquid solvent/eluate may be forced out (drained from) of vessel V through prime input PIN.

Before vessel V is filled with liquid solvent, a vacuum may be applied to the gas/vacuum input of FIG. 5 where air or gas is sucked out of the vessel. The check valve prevents liquid solvent from being sucked into the vacuum pump when vacuum is applied to the gas/vacuum input of FIG. 5. During vacuum priming, check valve CV opens allowing air/gas to be sucked out of vessel V and liquid solvent to be sucked into vessel V through prime input P1. Since check valve CV is at the top of vessel V, the vacuum pump will not suck liquid solvent through nozzle N into the vacuum pump, instead liquid solvent will flow into vessel V until the vacuum is shut off.

Nozzles may include a check valve that opens when a gas is provided to an input and that closes when the pressure between an inner portion and a portion outside of the nozzle equalizes. Such nozzles may also close whenever pressure outside of the nozzle is greater than pressure inside the nozzle. Check valves incorporated into a nozzle may also be spring loaded.

In an example, a nozzle may be initially an un-deployed state, then a fluid, liquid, or gas may be provided to an input of the nozzle that causes the nozzle to move or extend, when a pressure reaches a desired pressure, the nozzle may fully deploy and release gas into the vessel. In certain instances the desired pressure may be a pressure difference between the pressure within the hopper and the pressure of the supplied fluid. The vacuum pump may be used to maintain a pressure gradient. The nozzle may retract when the pressure difference between the internal vessel pressure and the pressure provided to the nozzle is less than a pressure capable of deploying the nozzle. In such an instance, the nozzle may be spring loaded, may be hydraulically loaded, and/or be loaded by gravity such that the nozzle withdraws when the pressure differential abates.

Figure 6A:
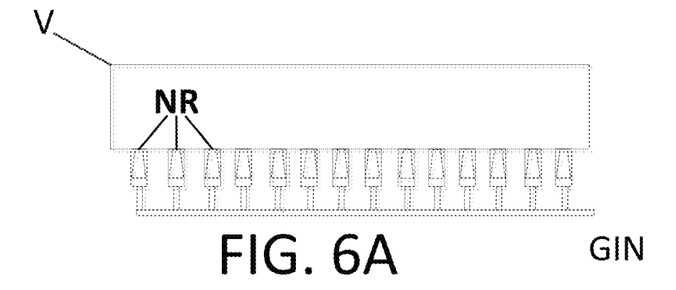
FIGS. 6A and 6B illustrate a vessel in which nozzles are dispersed along a bottom surface of a vessel.
Figure 6B:
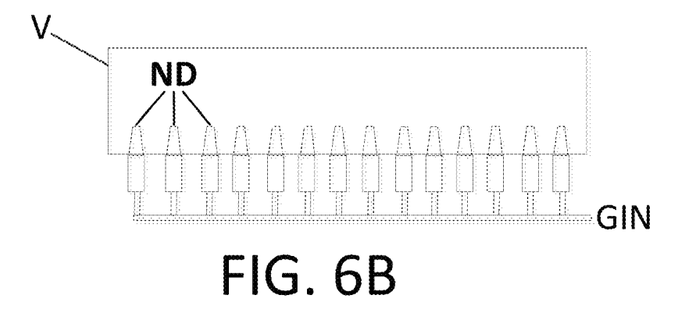

FIGS. 6A and 6B illustrate a vessel in which nozzles are dispersed along a bottom surface of a vessel. FIG. 6A illustrates vessel V where nozzles are a non-deployed or retracted state NR with a fluid input GI. FIG. 6B illustrates the nozzles of FIG. 6A in a deployed state ND. The nozzles of FIGS. 6A and 6B may deploy when pressurized fluid is applied to fluid input GIN. Such a configuration could be used with performing extractions or when drying plant matter, including when drying previously extracted plant matter. The nozzles of FIGS. 6A and 6B may include one or more holes through which gas or fluids flow through. Additional nozzles may also be disposed along top or side surfaces of vessel V.

Fluid nozzles may also be deployed along surfaces of a vessel to aid in extraction or drying in stationary configurations, where the nozzles do not deploy. In such instances, nozzles may be mounted on any surface of a vessel, including the bottom surface, a top surface, or be inserted into a vessel. Such configurations may appear similar to the nozzles of FIG. 6A, yet in a configuration where the nozzles do not deploy. In yet other instances, nozzles may not be deployable, yet may be simply affixed/attached to a surface of an extraction vessel.

In certain instances, the nozzle may be inserted in a cylindrical extraction apparatus or in a cross section of pipe. The nozzle may transport solvent, a gas, or both solvent and gas. The nozzle may include a first part that provides solvent and a second part that provides gas. In preferred embodiments, the gas provided does not include oxygen, such as an inert gas like nitrogen. Even so, oxygen may be present during an extraction, even though the presence of oxygen may not be preferred. While any gas may be used gasses other than oxygen are preferred because they prevent combustion. As such, these gasses may include or be nitrogen, helium, carbon dioxide, or other gasses. The gas may be provided by a pressurized cylinder. A preferred plant matter includes cannabis plant matter. Preferred solvents include, yet are not limited to hexane, n-hexanes, cyclohexane, ethanol, and heptane.

In certain instances a plurality of nozzles may be placed in an extraction or in a drying apparatus. The nozzles may include a quick connect that allows them to easily be removed from an apparatus. One or more nozzles may be placed into filter baskets and plant matter may be filled around the nozzles. In other instances a filter basked may be filled with cannabis plant matter and a nozzle may then be forced into or screwed into the plant matter prior to an extraction. The filter baskets may then be placed in an extraction vessel and the nozzle may be connected to gas or solvent supplies using quick connects, after which the extraction vessel may be sealed and an extraction performed.

Nozzles may transfer gas into an apparatus, increasing pressure in a vessel. When the vessel includes plant matter and liquid solvent, the gas may forcibly percolate through the plant matter stimulating extraction of essential elements in the plant matter. As mentioned above, nozzles may pass both solvent and gas through one or more nozzle portions.

Figure 7:
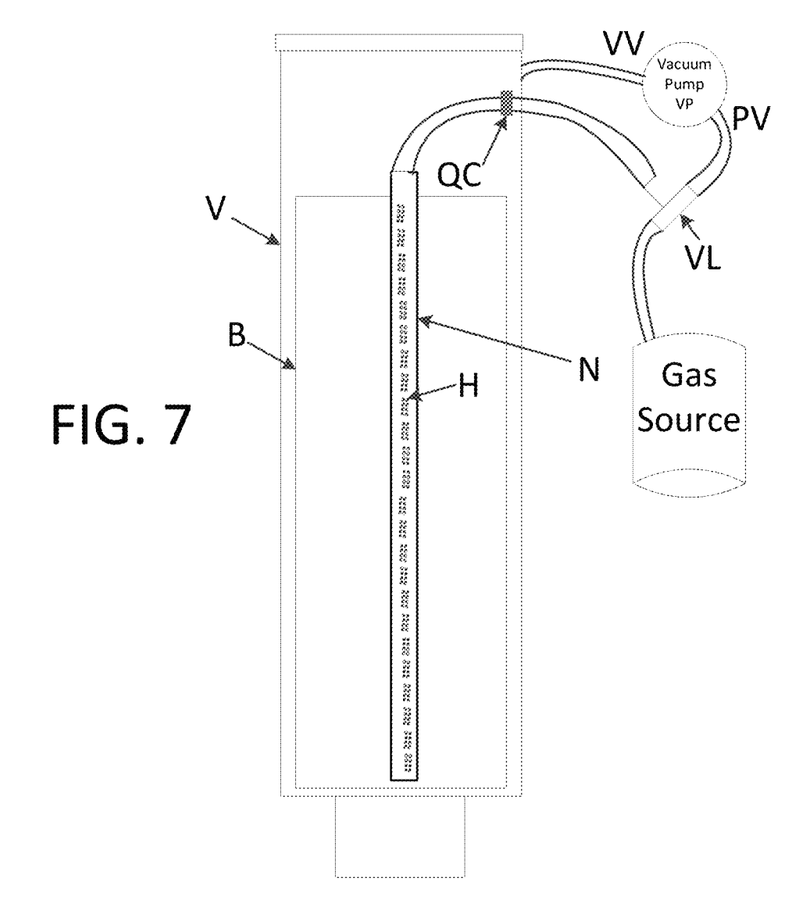
FIG. 7 illustrates a nozzle configured to introduce and recirculate gasses through an extraction vessel.

FIG. 7 illustrates a nozzle configured to introduce and recirculate gasses through an extraction vessel. FIG. 7 includes vessel V, basket B, nozzle N with holes H, a gas cylinder and a vacuum pump. Note that the gas cylinder and vacuum pump VP are coupled to plumbing connector VL. Plumbing connector VL may include one or more valves or may be simply a connection tee. Note also that nozzle N is coupled via quick connector QC via plumbing that connects nozzle N to plumbing connector VL. Vacuum VP includes a vacuum side VV and a vacuum pressure side VP.

While not illustrated in FIG. 7, vessel V or basket B may be filled with plant matter, such as cannabis plant matter. Vessel V may then be closed, and a vacuum pump may be used to remove air/oxygen from vessel V, after which vessel V may be predominantly filled with liquid solvent. A head space free of liquid solvent may be maintained above basket B. After vessel V may then be predominantly filled with liquid solvent a gas (such as nitrogen) may be introduced into vessel V from gas cylinder and plumbing connector VL to desired pressure. After vessel V has been topped off with gas, vacuum pump VP may recirculate that gas through nozzle N. In such an instance, the vacuum pump VP may suck gas from the top of vessel V into vacuum input VV. Gas may then be provided to nozzle N and provide gas via vacuum pump output PV, plumbing connector VL via vacuum pump output PV, plumbing connector VL, through plumbing that includes quick connect QC, and through nozzle N holes H. When such a recirculation of gas occurs solvent soaked play matter will be agitated by gas bubbles escaping from nozzle N via holes H.

Later after vessel V has been drained of liquid solvent, gas may be circulated through vacuum pump VP and the holes H in nozzle N to dry the plant matter. While not depicted in FIG. 7, a solvent trap may be attached to vacuum pump VP to condensate solvent vapor and trap it in the solvent trap during this drying step. In such an instance, the solvent trap may be located between vacuum pump output PV and plumbing connector VL, for example. Alternatively or additionally vacuum pump VP may be coupled to other apparatus, such as an additional gas storage vessel or be vented to the atmosphere when appropriate or desired.

Nozzles may include pointed surfaces that allow them to be inserted into and through plant matter in a vessel. Alternatively or additionally nozzles may be spiral shaped or include spiral shaped features that allow them to progressively move through plant matter as they are inserted, in such instances these nozzles may be screwed in with a rotational force or those nozzles may rotate as they are inserted into plant matter. As such, nozzles may also be coupled to tubing or pipes that allow the nozzle to rotate via a rotational coupling, for example.

In yet other instances one or more filter baskets may include extraction nozzles and a plant slurry may be pumped into the filter baskets where the filter baskets separate plant matter from the solvent eluate. In such alternate configurations the plant matter may be pumped into a vessel where nozzles are located and extraction and/or drying may be performed. After the eluate is removed or predominantly removed, the plant matter may be dried using methods consistent with the present disclosure. Filter baskets may include filter socks that filter the plant matter from the eluate or include stainless steel screens with preferred hole sizes. In certain instances plant matter may be placed in or pumped into large vessels of any shape. Vessels may include arrays of nozzles that may be built into a vessel or inserted into a vessel. Nozzles or nozzle holes may include screening or filters that help prevent plant matter from migrating into an inside surface of a nozzle. Such screening or filters may be of any size.

A method for extracting essential elements from plant matter may include the following steps or may include a subset of the following steps. First of all plant matter may be placed in or pumped into an apparatus that includes one or more nozzles. A vacuum pump may be used to provide at least a partial vacuum in the apparatus. The vacuum pump may be used to prime the apparatus with solvent from a solvent tank. A gas may then be introduced through the one or more nozzles. Solvent pumps may also pump solvent or a plant matter solvent slurry.

As mentioned above, solvent may be pumped through a nozzle. The gas and the solvent may be introduced or recycled into the apparatus through one or more individual nozzles. The nozzles may introduce the gas though one particular nozzle (or nozzle portion) and solvent may be introduced through a second particular nozzle (or nozzle portion). A nozzle may include separate elements that provide gas or liquid solvent. Gas may be introduced into the apparatus until the vessel is pressurized to a target pressure level, after which pressure in a hopper/vessel may be vented, vented into another chamber, or coupled through solvent trap and a vacuum pump. Best practices of the method may limit or prevent venting of gasses to the environment whenever possible and practical. In certain instances safety vents may vent vessels associated with an apparatus.

In certain instances a sonic or ultrasonic transducer may be coupled to a nozzle. Nozzles may be designed to resonate as a gas is passed through the nozzle without using a sonic/ultrasonic transducer. As such, nozzles may generate sonic or ultrasonic waves as that nozzle resonates. A nozzle may, therefore, act like a whistle, a flute, an organ, or as another type of gas driven musical instrument or dog whistle. Sonic or ultrasonic waves generated by such nozzles combined with gas bubbles may act to extract matter from plants, such as cannabinoids from cannabis plant matter, for example.

Vessels used with methods and systems of the present disclosure may be of any shape, cylindrical, square, rectangular, triangular, or other. Such vessels may also include multiple compartments, such as a multi-bag filtration system that includes multiple cylindrical compartments filters or filter bags. In such instances one or more nozzles may be installed in a vessel. Gasses may be introduced through a nozzle from a pressurized tank and then may be recirculated through a vessel and nozzle with a vacuum pump. A solvent trap may be coupled to a vacuum pump that recirculates gas, such as an inert gas like nitrogen or other gas like carbon dioxide. A solvent trap may include or be coupled to a chilling element. Chilled liquid may be passed through the solvent trap or may include a thermos-electric chilling device.

Such safety venting may occur into a volume liquid (including water or solvent) or through a solvent trap (such as a Wolfe bottle or a chilled condensation device). Such controlled venting may help limit or prevent solvent rich vapors from being released into the atmosphere. The volume of water may be placed in a vessel that is open to the environment such that trace solvent condensate that may condense in the water be contained and not enter the atmosphere. Safety vents may be pressure activated and release when exposed to a pressure differential of a magnitude capable of releasing the safety vent valve.

A vacuum pump coupled to a solvent trap may suck gas from the apparatus while condensing liquid solvent in the solvent trap. The output of the vacuum pump may be coupled to a nozzle such that gas recirculates from the apparatus, through the solvent trap, through the vacuum pump, and then back into the apparatus. The output of the vacuum pump may also be connected to an input a secondary vessel where the gas may be pressurized before it is re-introduced into the apparatus. In such an instance, a method consistent with the present disclosure may cycle pressure in the apparatus from a lower pressure to a higher pressure. Pressures may be cycled from a complete or nearly complete vacuum to pressures significantly higher that atmospheric pressure. In such instances, a hopper (or vessel) containing plant matter (such as cannabis plant matter) could be dried by re-circulating gas from the hopper through the solvent trap, through the vacuum pump, optionally through a secondary vessel, and back into the hopper. Over time cannabis plant matter could be dried. This drying may occur after all or most liquid solvent has been removed from the hopper.

Plant matter may be dry plant matter or may be plant matter that has been freshly cut down (i.e. be plant matter that still contains water, i.e. wet plant matter).

Liquid or eluate from the hopper may be passed through an evaporator, such as a rotary evaporator, a thin film film/wet film evaporator, or other evaporator to remove essential elements, such as cannabinoids, flavonoids, or terpenes from the liquid/eluate after extraction.

A solvent trap of the present disclosure may be a Wolfe bottle, may include a chilled condenser, or may include an element through which a cooling liquid is pumped from a chiller. A sensor coupled to a processor may be used to monitor an amount of solvent vapor in the hopper. In such an instance, when sensor data indicates that an amount of solvent vapor is below a threshold solvent vapor threshold level, the plant matter may be identified as being "dry" or "dry enough," indicating that a drying process is complete.

Pressures greater than the auto-ignition pressure of a particular solvent in normal atmospheric conditions may be avoided. For example, if a gas has an auto-ignition pressure of 50 pounds per square inch (psi), pressures in a vessel associated with the apparatus may be limited to less than 50 psi. Furthermore, an alarm may be issued if pressure in a particular increases above a threshold level. In certain instances when a pressure of concern is approached or reached a computer coupled to a sensor may command one or more valves to open or close. Such precautions could prevent the possibility of solvent rich pressurized gasses leaking from a vessel approaching conditions where auto-ignition or other concerns related to the solvent could occur. Here again the pressure could be vented into the atmosphere or into another container.

In instances where a particular nozzle is controllably coupled to a vacuum and to a gas supply (such a nitrogen tank, or other vessel) the nozzle or a portion of the hopper could be coupled to a check valve. The check valve when positioned above a level of liquid solvent would allow vacuum priming of the hopper with liquid solvent without drawing suction through a portion of the nozzle. In such an instance, when vacuum is applied the check valve would open allowing air or gas to be sucked out of the hopper and liquid solvent to be sucked into the hopper from a solvent tank. The solvent tank and the hopper may be coupled with a valve. The check valve helps prevent liquid solvent and plant matter from being sucked into the nozzle. Later when the vacuum is removed, a gas (such as nitrogen) could be supplied to the nozzle and the check valve would close, forcing the gas through the nozzle and into the plant matter. In alternate embodiments vacuum pumps, the hopper, a solvent tank, secondary tanks, solvent traps, and a supply of gas may be controllably connected with valves (manual or computer controlled; pneumatic or electrically actuated) that isolate connections between various parts of an apparatus. Since check valves used for priming solvent in a vessel will be forced closed when pressurized gas is provided to the check valve and will open when vacuum is provided to the check valve, such check valves incorporated into a system may not be spring loaded or be spring loaded with a weak spring.

Figure 8:
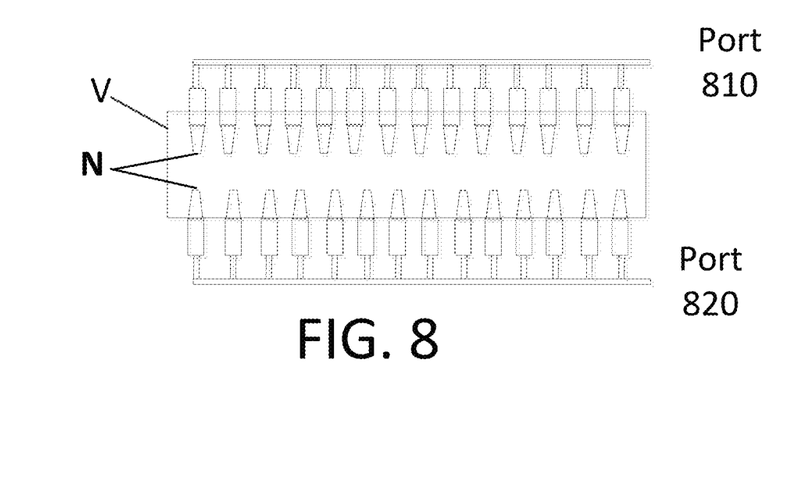
FIG. 8 illustrates an extraction chamber with nozzles at different levels within a vessel.

FIG. 8 illustrates an extraction chamber with nozzles at different levels within a vessel. FIG. 8 includes an upper and a lower set of nozzles N in a vessel V, where the upper set of nozzles are coupled to port 810 and the lower set of nozzles are coupled to port 820. Plant matter may be placed in vessel V or may be pumped into vessel V when plant material is processed. When plant matter is pumped into vessel V, it may be pumped with a pump capable of moving a slurry of plant material and solvent through a pipe not illustrated in FIG. 8.

Fluids, such as liquid solvent or gasses may be introduced and removed from vessel V either via port 810 or port 820, or via both ports. Different solvents may be passed in vessel V at different times. For example, a first type of solvent may be passed into vessel V via one or both of nozzles 810/820 and after an extraction is performed with the first solvent, a second solvent may be introduced into vessel V. Plant materials may be may be stimulated with gas introduced into vessel V through some or all nozzles N when an extraction or post extraction process is being performed. Two exemplary solvents are ethanol and n-hexane that may separate into layers where lighter plant derived materials and n-hexane may separate from heavier materials such as the ethanol or other materials. In such an instance, the different solvents may be chilled or heated. Water may also be added into vessel V, further stimulation may be performed, and then the materials may be allowed to separate into three levels. These three levels may include a water level of water and water born materials, an ethanol layer that includes ethanol, and an n-hexane level that may include cannabinoids or other lighter materials.

Materials may be drawn from any level via nozzles. For example an eluate may be drawn from a top level via port 810, and other materials may be drawn from a lower level via port 820, or materials may be drawn from both the top and the bottom layer at the same time. Nozzles may be dispersed on the sides of vessel V or different nozzles may be dispersed at multiple different levels within vessel V. Sensors may also be included in vessel V that may sense different types of substances or that can help discriminate between two or more elements or element densities when detecting n-hexane, ethanol, or water for example. These sensors may be coupled to a control system when elements consistent with a particular layer are drawn out of vessel V.

Methods and apparatus consistent with the present disclosure may include vessel V of FIG. 8 receiving an eluate that includes solvent and essential elements extracted from plant matter. The essential elements may have been extracted from plant matter by any means, for example, by $CO_2$ extraction, hydrocarbon extraction, or extraction using any solvent, including yet not limited to alcohol, ethanol, hexane, ether, heptane, pentane, butane, or propane. An extract formed by an extraction process may be combined with a solvent that is liquid at room temperatures and pressures to form an eluate or the eluate may have been formed during an initial extraction process. In an example, a concentrate extracted using $CO_2$ may be combined with alcohol or hexane to form an eluate and that eluate may be provided to vessel V. In certain instances, another solvent may then combined with the eluate. Here again different layers may be formed, a layer that includes hexane and lighter elements and a layer that includes alcohol and other elements. Water may then be added, creating a third layer that includes water and water soluble materials. Nozzles in vessel V may provide the eluate or solvents. A gas or fluid may be moved into or pumped into vessel V to facilitate mixing of materials after which, a circulation gas may be halted and layers may be allowed to form. Nozzles N of FIG. 8 may then be used to draw an eluate from a top level via port 810, or other materials may be drawn from a lower level via port 820.

Nozzles consistent with the present disclosure may cause substances within a vessel to be circulated in a circular direction horizontal to a vertical axis or in other directions, such as in a vertical directions. Nozzles may be controlled to switch the direction of a flow. As such flow changes may change from a clockwise rotation to a counter clockwise direction or to a vertical circulatory path. These directional changes may change by a control system that opens certain valves and that closes other valves, where each of those valves couple to specific nozzles that are pointed in certain specific directions. Alternatively or additionally, nozzles may be coupled to one or more actuators that move the nozzles to point in a particular direction. Control systems consistent with the present disclosure may include sensors, a memory, and a processor.

Nozzles may be used to provide a fluid from a source such as a tank that stores liquid nitrogen. In such an instances liquid nitrogen may be introduced into a chamber that includes plant material to cool or freeze plant matter before, after, or at a time when a solvent is provided to the chamber. In such instances, for example, cannabis plant material may be chilled or frozen and a solvent may then extract essential elements from the cannabis plant matter. Here again the chamber may include a plurality of nozzles, one or more elongated nozzles, or other nozzles disposed in a chamber as previously discussed. In certain instances, the solvent provided to the chamber may be at a different temperature, for example, at a temperature that is warmer than the chilled plant matter. In such instances, the temperatures internal to the chamber or of the introduced solvent may be controlled. Furthermore, such temperatures may thermally shock the plant matter according to a process that changes the temperature of cannabis plant matter by more than a threshold amount. For example, cannabis plant matter at an initial temperature may be placed in an extraction chamber, excess gas may be removed from the chamber (using a vacuum pump for example), nitrogen in a fluid (liquid or gas) state may be introduced into the chamber to chill the plant matter to a particular temperature or temperature change (initial temperature—target delta/change in temperature), and then a solvent at yet another temperature may be introduced. As such, methods consistent with the present disclosure may include one or more changes in temperature. Such methods may also use nozzles to distribute fluids through a crosssection of plant material in an extraction chamber as temperatures are changed by a series of temperature changes. Temperatures inside of an extraction chamber may be monitored using one or more sensors coupled to a controller configured to open and close valves or actuate pumps when fluids of various sorts are provided to a chamber in controlled ways.

After an initial extraction, plant matter or extracted materials may be processed using methods discussed within this disclosure. For example, solvent saturated plant matter may be dried such that a threshold level of solvent is removed from plant matter. When drying solvent saturated plant matter a sensor that senses solvent vapors of the presence of solvent in a portion of plant matter may be used to identify when a drying process is complete. For example, drying could be complete when sensor data indicated that vapor solvent level is measured to meet or be below a threshold concentration (for example 1 part per million).

Alternatively extracts formed by any method may be combined with one or more solvents, where nozzles may be used to stimulate or remove materials from specific locations within a vessel. Alternatively a solvent could be provided to the chamber and nitrogen fluid (liquid or gas) could be provided to the chamber or solvent and nitrogen fluid could be provided to a chamber at the same time. Here again temperatures could be controlled such that an extraction is performed at a preferred temperature. Such extractions could be performed using either low or high temperatures according to a desired extraction protocol.

In instances where an extraction has been performed and where an eluate is contained within a chamber the eluate may be chilled by providing a fluid in a cryogenic state that chills the eluate. For example, liquid nitrogen could be provided to a vessel. In such an instance the liquid nitrogen could be evaporate into nitrogen gas that is circulated through nozzle in the vessel when an extraction is performed or during a process that dries solvent saturated plant matter. As such, the nozzle could be used to percolate nitrogen gas through solvent saturated plant matter during or after an extraction process. This could be performed when the eluate is in a chamber that does not include the raw post extracted plant matter. Multiple different solvents could be provided to this chamber and separations could be performed. Here again two or three different liquids could be provided, for example, two or more different liquids could include hexane and alcohol, alcohol and water, or hexane-alcohol-and water.

Figure 9:
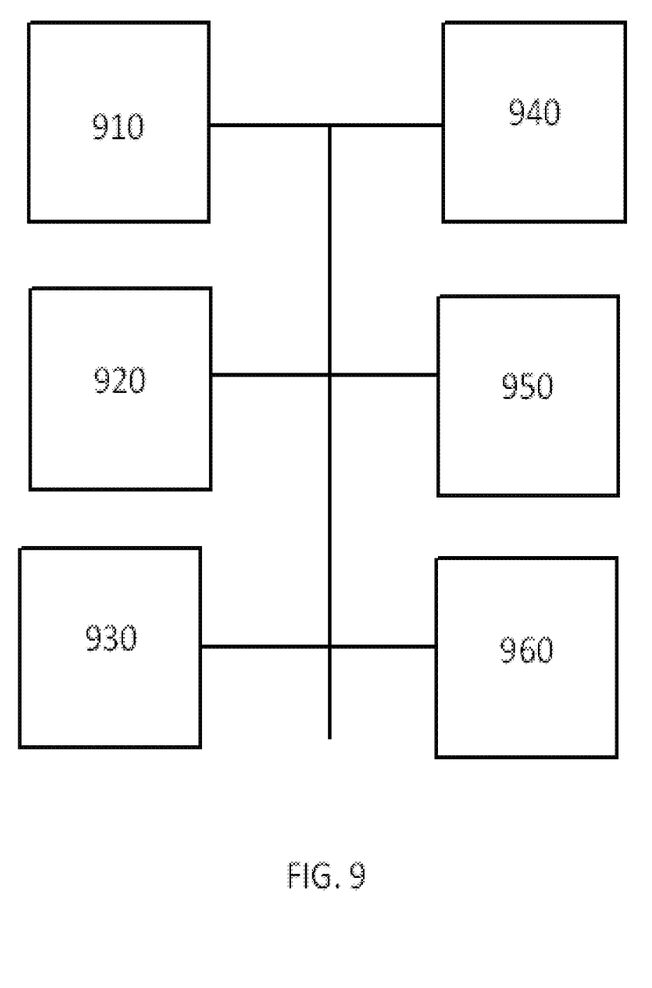
FIG. 9 illustrates a control system that may be used to control extraction and evaporation/concentration systems and methods consistent with the present disclosure.

FIG. 9 illustrates a control system that may be used to control extraction and evaporation/concentration systems and methods consistent with the present disclosure. FIG. 4 includes controller/processor 910 that may execute instructions out of memory 920. FIG. 4 also include mass data store 930, network interface 940, wireless communication interface 950, and input/outputs (I/O) 960. Processor 910 may receive information from sensors via network interface 940, via wireless communication interface 940, or from I/O 960 when monitoring actions performed by an extraction and/or a evaporation/concentration system.

The computer FIG. 9 may reside with an evaporation or extraction system or may be remote from such systems. In certain systems computing devices such as a desktop, notebook, tablet, or cell phone computing device may be used to control or adjust the control of extraction or evaporation/concentration systems from a remote location. In such instances network interface or wireless communication interface may communicate with a remote computing device. A remote computing device consistent with the present disclosure may display a user interface where sensor data may be observed or that may be used to control the operation of systems consistent with the present disclosure. Such a user interface may be used to control a motor, a rotational speed, vacuum pressures, vacuum pumps, valves, flow rates, or to shut down an extraction or evaporation/concentration system consistent with the present disclosure. Wired network connections may include any standard wired network known in the art (Ethernet for example). Wireless communications may include communication signals consistent with cell phones, with 802.11 Wi-Fi, Bluetooth, radio, or other wireless communication medium.

Extraction systems consistent with the present disclosure may extract essential elements from plant matter, that may be dry plant matter or may be plant matter that has been freshly cut down (i.e. be plant matter that still contains water, i.e. wet plant matter). Liquid or eluate from a hopper may be passed through an evaporator, such as a rotary evaporator, a thin film film/wet film evaporator, or other evaporator to remove essential elements, such as cannabinoids, flavonoids, or terpenes from the liquid/eluate.

What is claimed is:

1. A method for processing plant matter, the method comprising:
    filling at least a portion of a vessel with the plant matter, the vessel including an elongated nozzle extending from an upper portion of the vessel, through a central portion of the vessel, and to a lower portion of the vessel, the elongated nozzle including a plurality of holes distributed along the elongated nozzle for passing a fluid from an inside portion of the nozzle to an outside portion of the nozzle when the plant matter is processed;
    introducing the fluid to the upper portion, the lower portion and the all central portion of the vessel based on the distribution of the plurality of holes;
    introducing solvent into the vessel to extract an element from the plant matter; and
    outputting at least a portion of the extracted element from inside the vessel to outside the vessel via a first port at the vessel.

2. The method of claim 1, further comprising pumping the fluid from an output port at the vessel to an input port at the vessel, the input port coupled to the nozzle.

3. The method of claim 1, wherein the fluid includes nitrogen that is sourced from a container that contains liquid nitrogen.

4. The method of claim 3, further comprising removing at least a portion of oxygen from the vessel before passing the fluid from the inside portion of the nozzle to the outside portion of the nozzle, the fluid chilling the plant matter based on the fluid being sourced from the container that contains the liquid nitrogen.

5. The method of claim 1, wherein the fluid cools at least a portion of the plant matter based on the fluid being introduced to the central portion of the vessel.

6. The method of claim 1, wherein the nozzle is longer than it is wide and the fluid passes through the plant matter based on the plurality of holes being distributed along the nozzle from the lower portion, the central portion, and the upper portion of the vessel.

7. The method of claim 6, wherein the fluid includes nitrogen gas provided from a nitrogen tank.

8. The method of claim 1, wherein the fluid is liquid nitrogen that evaporates into a gaseous form.

9. The method of claim 1, further comprising measuring at least one of a pressure or a temperature of an inside portion of the vessel with a sensor communicatively couple with an electronic control system and the plant matter is from a *cannabis* plant.

10. The method of claim 1, further comprising:
    vaporizing a portion of the solvent from the plant matter by pumping the fluid from an output port at the vessel to an input port at the vessel, the input port coupled to the nozzle; and
    condensing the vaporized portion of the solvent in a solvent trap.

11. The method of claim 10, further comprising:
    receiving sensor data at an electronic control system that senses the vaporized solvent;
    identifying a density of the vaporized solvent; and
    identifying that the plant matter is dried based on the density of the vaporized solvent being below a threshold amount.

12. The method of claim 10, further comprising:
    receiving sensor data at an electronic control system that senses an amount of residual solvent absorbed in at least a portion of the plant matter; and
    identifying that the plant matter is dried based on sensor data indicating that the residual solvent absorbed in the at least portion of the plant matter is below a threshold level.

13. The method of claim 1, further comprising, pumping a portion of an eluate from the vessel through nozzle.

14. The method of claim 13, wherein the nozzle includes a first input that passes the fluid and a second input that that passes the portion of the eluate.

15. The method of claim 1, further comprising passing the fluid through a second nozzle.

16. The method of claim 1, further comprising introducing a second solvent into the vessel, wherein the second solvent is a different type of solvent than the solvent, and the solvent and the second solvent form separate layers within the vessel based on the second solvent and the solvent being the different types of solvent.

17. The method of claim 1, wherein the solvent includes carbon dioxide (CO2).

18. The method of claim 1, wherein the fluid is a same type of material as the solvent.

* * * * *